(12) United States Patent
Seifert et al.

(10) Patent No.: US 6,175,018 B1
(45) Date of Patent: Jan. 16, 2001

(54) PROCESS FOR PREPARATION OF PROPIONIC ACID DERIVATIVES

(75) Inventors: Gottfried Seifert, Magden; Andrea Rolf Sting, Gipf-Oberfrick; Bernhard Urwyler, Therwil, all of (CH)

(73) Assignee: Novartis Crop Protection, Inc., Greensboro, NC (US)

( * ) Notice: Under 35 U.S.C. 154(b), the term of this patent shall be extended for 0 days.

(21) Appl. No.: 09/270,925

(22) Filed: Mar. 16, 1999

(30) Foreign Application Priority Data

Mar. 24, 1998 (CH) .................................... 687/98

(51) Int. Cl.[7] ............... C07D 213/64; C07D 213/643
(52) U.S. Cl. ........................... 546/302; 546/301
(58) Field of Search ................... 546/301, 302

(56) References Cited

U.S. PATENT DOCUMENTS 5,002,604   3/1991   Schurter et al. ............. 71/94

FOREIGN PATENT DOCUMENTS

| 592804 | 12/1987 | (AU) . |
| 0 083 556 | 7/1983 | (EP) . |
| 0 248 968 | 12/1987 | (EP) . |
| 0 439 857 | 8/1991 | (EP) . |

OTHER PUBLICATIONS

Ettlinger MG, et al. "The Mustard Oil of Rape Seed, Allylcarbinyl Isothiocyanate, and Synthetic Isomers" J Am Chem Soc, 77, pp. 1831–1836 (1955).
J. Chem. Res. Miniprint 7, 1992, pp. 1601–1615.
Ann. Chim. (Paris) 13, No. 1, 1956, pp. 161–213.
J. App. Chem. USSR, 65, No. 12.2, 1992, pp. 2310–2314.
J. Med. Chem. 20, No. 12, 1977, pp. 1584–1588.
Heterocycles, 32, No. 10, 1991, pp. 1947–1953.

*Primary Examiner*—Alan L. Rotman
(74) *Attorney, Agent, or Firm*—Michael P. Morris; William A. Teoli, Jr.

(57) ABSTRACT

(R)(+)-2-[4-(5-chloro 3-fluoropyridin-2-yloxy)-phenoxy]-propionic acid propinyl ester is produced by converting a compound of formula II

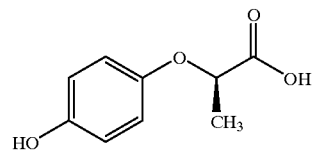
(II)

in an inert organic solvent, without isolation of the intermediate products, with $M_2CO_3$, in which M is sodium or potassium, into the compound of formula III

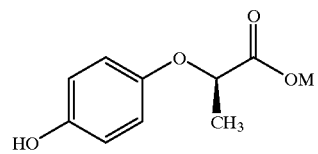
(III)

reacting this with the compound of formula IV

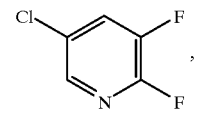
(IV)

to form the compound of formula V

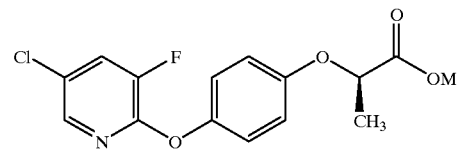
(V)

and converting this with a compound of formula VI

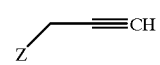
(VI)

wherein Z signifies phenylsulphonyl, tosyl, methylsulphonyl, nosyl, bromophenyl, Cl-, Br- or ClCO-, into the compound of formula I.

1 Claim, No Drawings

PROCESS FOR PREPARATION OF PROPIONIC ACID DERIVATIVES

The present invention relates to a process for the preparation of (R)(+)-2-[4-(5-chloro-3-fluoropyridin-2-yloxy)-phenoxy]-propionic acid propinyl ester.

(R)(+)-2-[4-(5-chloro-3-fluoropyridin-2-yloxy)-phenoxy]-propionic acid propinyl ester possesses herbicidal activity and is described for example in EP-A-0 248 968. [4-(5-chloro-3-fluoropyridin-2-yloxy)-phenoxy]-propionic acid derivatives may be produced for example in accordance with EP-A-0 439 857, by reacting 5-chloro-2,3-difluoropyridine with corresponding 4-hydroxypropionic acid esters in the presence of a water-free base and in the absence of a solvent. However, this process is unsuitable for producing (R)(+)-2-[4-(5-chloro-3-fluoropyridin-2-yloxy)-phenoxy]-propionic acid propinyl ester, since the triple bonding of the hydroxypropionic acid ester is inclined to form polymers under the conditions of the process and under basic conditions. In addition, this process is especially problematic as regards the safety aspect, since the reaction mixture can only be heated without solvents at some risk, owing to the high thermal potential of this triple bond.

According to EP-A-0 248 968, pages 12 to 14, (R)(+)-2-[4-(5-chloro-3-fluoropyridin-2-yloxy)-phenoxy]-propionic acid propinyl ester is obtained whereby a) in a first step, a compound of formula A

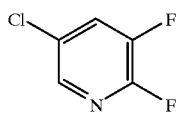
(A)

in dimethyl sulphoxide is reacted with a mixture of hydroquinone and potassium hydroxide in dimethyl sulphoxide to form a compound of formula B

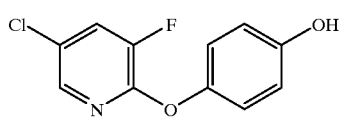
(B)

this compound b) in a second step, in dimethyl sulphoxide, is reacted in the presence of potassium carbonate with S(−)-lactic acid methyl ester tosylate to form the compound of formula C

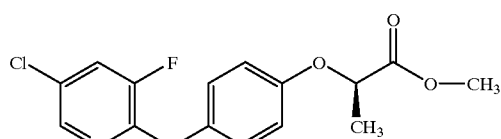
(C)

this compound c) in a third step, in dioxane, is reacted in the presence of sodium hydroxide solution to form the compound of formula D

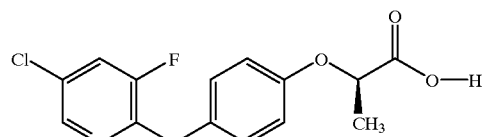
(D)

this compound d) in a fourth step, in toluene, is reacted with thionyl chloride to form the compound of formula (E)

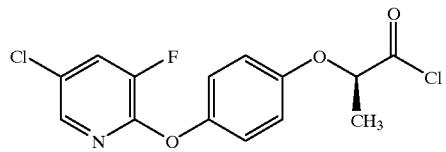
(E)

which finally, without further isolation, this compound e) is reacted with a mixture of triethylamine and propinol in toluene to form (R)(+)-2-[4-(5-chloro-3-fluoropyridin-2-yloxy)-phenoxy]-propionic acid propinyl ester.

This process has the major disadvantage that, because of the four-stage reaction procedure, complicated separation and purification steps are necessary. This leads to substantial losses of yield. In addition, while the process is being carried out, the solvent has to be changed twice. This necessitates additional time-consuming and expensive distillation steps. The known process is therefore not the optimum one especially for application on a large scale.

The aim of the present invention is therefore to provide a process which enables (R)(+)-2-[4-(5-chloro-3-fluoropyridin-2-yloxy)-phenoxy]-propionic acid propinyl ester to be produced in a more simple manner, in higher purity and in higher yields.

It has now been found that (R)(+)-2-[4-(5-chloro-3-fluoropyridin-2-yloxy)-phenoxy]-propionic acid propinyl ester of formula I

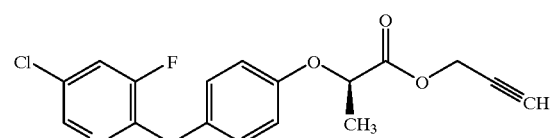
(I)

can be produced in a particularly advantageous manner by converting a compound of formula II

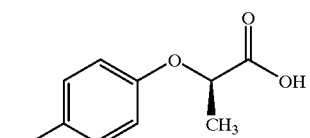
(II)

in an inert organic solvent, without isolation of the intermediate products, with $M_2CO_3$, in which M is sodium or potassium, into the compound of formula III

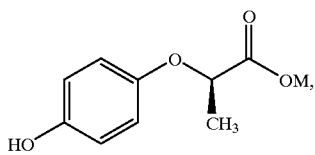

wherein M is sodium or potassium, reacting this compound with the compound of formula IV

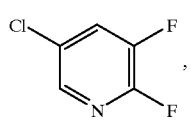

to form the compound of formula V

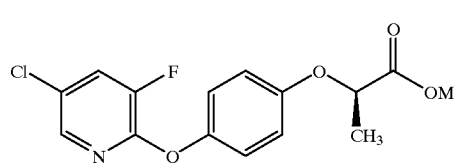

wherein M is sodium or potassium, and converting this compound with a compound of formula VI

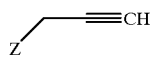

wherein Z signifies a leaving group such as phenylsulphonyl, tosyl, methylsulphonyl, nosyl, bromophenyl, Cl-, Br- or ClCO-, into the compound of formula I.

The starting compounds may be used in stoichiometric quantities. It is preferable to use the compound of formula IV in an excess of 0.05 to 0.3 equivalents, most preferably 0.1 equivalents, based on the compound of formula III. The compound of formula VI is preferably employed in an excess of 0.05 to 0.15 equivalents.

Within the scope of the present invention, M in $M_2CO_3$ is preferably potassium.

Suitable inert organic solvents within the scope of the present invention are in particular ketones, esters and ethers. Dimethyl formamide, dimethyl sulphoxide, N-methyl pyrrolidone or acetonitrile are especially suitable as solvents. Dimethyl formamide and acetonitrile are preferred in particular, most preferably dimethyl formamide. In a preferred embodiment of the process according to the invention, in formula VI, Z is chlorine. The process according to the invention can be carried out at elevated temperatures, especially at 40 to 120° C. A temperature range of 60° to 90 ° C., most preferably 70 to 75° C., is preferred.

The reaction of formula II with formula IV may be carried out in the presence of a phase transfer catalyst in order to speed up the reaction. Suitable phase transfer catalysts are for example quaternary ammonium salts, quaternary phosphonium salts or crown ethers.

The starting compounds of formulae II, IV and VI are known or may be produced by known processes. The compound of formula IV is described for example in EP-A-0 248 968, and the compound of formula II in EP-A-0 083 556. Compounds of formula VI, wherein Z is chlorine, may be produced for example according to J. Am. Chem. Soc. 77, 1831(1955), whereby suitable bases for this reaction are pyridine and preferably 5-ethyl-2-methylpyridine.

The process according to the invention is distinguished from known processes in particular by the fact that it can be carried out as a one-pot process without changing the solvent. In this way, not only is the expenditure on apparatus considerably lower, but by avoiding complex separation and distillation steps, there is also a substantial saving in time. In addition, the substantial reduction in solvent residues achieved with the process according to the invention is particularly advantageous from an ecological point of view. The lower thermal loading of the product reduces the formation of undesired by-products and the particularly selective course of the reaction enables a more precise dosaging of the reactants to be achieved, which in turn leads to a higher yield and a product with considerably improved purity.

PREPARATIVE EXAMPLES

Example P1

Preparation of (R)(+)-2-[4-(5-chloro-3-fluoropyridin-2-yloxy)-phenoxy]-propionic acid propinyl ester 182 g of (R)-2-(p-hydroxyphenoxy)-propionic acid 100% (1 mol) in 600 g of DMF are converted into the corresponding potassium salt by adding 69 g of potassium carbonate powder (0.5 mols) at 70° C. whilst cleaving the $CO_2$. To this solution are added 193 g of potassium carbonate powder (1.4 mols) and then, at a temperature of 70–75° C., 165 g of 5-chloro-2,3-difluoropyridine (1.1 mols) are added over the course of 30 minutes. After 4 hours, the compound of formula V thus obtained is reacted totally, by measuring in 86 g of propargyl chloride (1.15 mols) as a 60–70% toluene solution over the course of 2 hours directly, without isolation, at a temperature of 70–75° C., to form the (R)(+)-2-[4-(5-chloro-3-fluoropyridin-2-yloxy)-phenoxy]-propionic acid propinyl ester. The salts are filtered off, washed with 300 g of DMF in portions, and the filtrate is concentrated to the melt on a rotary evaporator under vacuum at a temperature of 120°C. The crude melt of the (R)(+)-2-[4-(5-chloro-3-fluoropyridin-2-yloxy)-phenoxy]-propionic acid propinyl ester is mixed at a temperature of 50°C. with 300 g of ethanol/water 9:1, seeded at a temperature of 30 to 35° C. and cooled to a temperature of 0 to 50° C. The crystal pulp is added to a suction filter, washed with 70 g of ethanol/water 9:1, and dried under vacuum at a temperature of 30 °C. 307 g of active substance are obtained with a content of 97 % (GC), corresponding to a yield of 85% of theory, based on (R)-2-(p-hydroxyphenoxy)-propionic acid.

Example P2

Preparation of (R)(+)-2-[4-(5-chloro-3-fluoropyridin-2-yloxy)-phenoxy]-propionic acid propinyl ester 182 g of (R)-2-(p-hydroxyphenoxy)-propionic acid 100% (1 mol) in 1500 g of acetonitrile are converted into the corresponding potassium salt by adding 69 g of potassium carbonate powder (0.5 mols) at 70°C. whilst cleaving the $CO_2$. Then, 193 g of potassium carbonate powder (1.4 mols) and 2 g of tetrabutyl ammonium bromide as the phase transfer catalyst are added to the reaction mixture, and at a temperature of 70 to 75° C., 165 g of 5-chloro-2,3-difluoropyridine (1.1 mols) are added over the course of 30 minutes. After 8 hours, the compound of formula V thus obtained is reacted totally, by measuring in 154 g of propargyl mesylate (1.15 mols) as a 60–70% toluene solution over the course of 2 hours, directly, without isolation, at a temperature of 70–75° C., to form the (R)(+)-2-[4-(5-chloro-3-fluoropyridin-2-yloxy)-phenoxy]-propionic acid propinyl ester. Working up is effected analogously to example P1. 304 g of (R)(+)-2-[4-(5-chloro-3-fluoropyridin-2-yloxy)-phenoxy]-propionic acid propinyl ester are obtained with a content of 98% (GC), corresponding to a yield of 85% of theory, based on (R)-2-(p-hydroxyphenoxy)-propionic acid.

Example P3

Preparation of (R)(+)-2-[4-(5-chloro-3-fluoropyridin-2-yloxy)-phenoxy]-propionic acid propinyl ester If the propargyl chloride of example P1 is replaced by 226 g (1.15 mols) of benzosulpho acid propargyl ester, 305 g of (R)(+)-2-[4-(5-chloro-3-fluoropyridin-2-yloxy)-phenoxy]-propionic acid propinyl ester are obtained with a content of 96%% (GC), corresponding to a yield of 84%% of theory, based on (R)-2-(p-hydroxyphenoxy)-propionic acid.

Example P4

Preparation of (R)(+)-2-[4-(5-chloro-3-fluoropyridin-2-yloxy)-phenoxy]-propionic acid propinyl ester 182 g of (R)-2-(p-hydroxyphenoxy)-propionic acid 100% (1 mol) in 1500 g of acetonitrile are converted into the corresponding potassium salt by adding 69 g of potassium carbonate powder (0.5 mols) at 70° C. whilst cleaving the $CO_2$. Then, 193 g of potassium carbonate powder (1.4 mols) and 2 g of tetrabutyl ammonium bromide as the phase transfer catalyst are added to the reaction mixture, and at a temperature of 70 to 75° C., 165 g of 5-chloro-2,3-difluoropyridine (1.1 mols) are added over the course of 30 minutes. After 8 hours, the compound of formula V thus obtained is reacted totally to form the (R)(+)-2-[4-(5-chloro-3-fluoropyridin-2-yloxy)-phenoxy]-propionic acid propinyl ester, directly, without isolation, at a temperature of 70–75° C., by measuring in chloroformic acid propargyl ester, whereby $CO_2$ is released. Working up is effected analogously to example P1. (R)(+)-2-[4-(5-chloro-3-fluoropyridin-2-yloxy)-phenoxy]-propionic acid propinyl ester is obtained with a content of 97% (GC), corresponding to a yield of 80% of theory, based on (R)-2-(p-hydroxyphenoxy)-propionic acid.

What is claimed is:

1. Process for the preparation of (R)(+)-2-[4-(5-chloro-3-fluoropyridin-2-yloxy)-phenoxy]-propionic acid propinyl ester of formula I

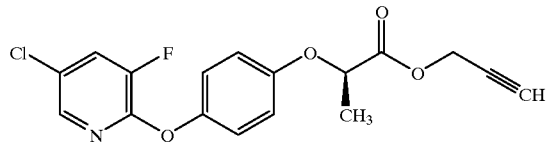

(I)

comprising converting a compound of formula II

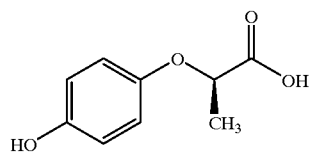

(II)

in an inert organic solvent, without isolation of the intermediate products, with $M_2CO_3$, in which M is sodium or potassium, into the compound of formula III

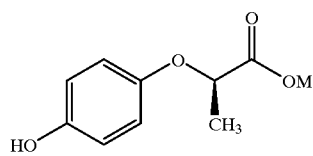

(III)

in which M is sodium or potassium, reacting this with the compound of formula IV

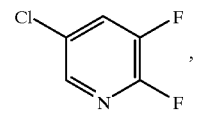

(IV)

to form the compound of formula V

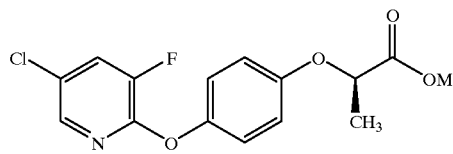

(V)

wherein M is sodium or potassium, and converting this compound with a compound of formula VI

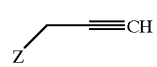

(VI)

wherein Z signifies phenylsulphonyl, tosyl, methylsulphonyl, para-nitrophenyl-sulfonyl, bromophenyl, Cl-, Br- or ClCO-, into the compound of formula I.

* * * * *